United States Patent [19]

Cieslak et al.

[11] 4,341,779

[45] Jul. 27, 1982

[54] ESTERS OF AMIDINEPENICILLINS

[75] Inventors: Jerzy Cieslak; Irena Busko-Oszczapowicz; Marek Stepniak, all of Warsaw, Poland

[73] Assignee: Tarchominskie Zaklady Farmaceutyczne, Warsaw, Poland

[21] Appl. No.: 67,278

[22] Filed: Aug. 17, 1979

[30] Foreign Application Priority Data

Sep. 8, 1978 [PL] Poland ................................ 209487
Apr. 13, 1979 [PL] Poland ................................ 214914

[51] Int. Cl.$^3$ ............................................ C07D 499/22
[52] U.S. Cl. ............................ 424/248.51; 424/267; 424/270; 424/248.55; 260/245.2 R; 542/420; 542/419

[58] Field of Search ............... 260/245.2, 245.2 R; 424/270, 248.55, 248.51, 267; 542/420, 419

[56] References Cited

U.S. PATENT DOCUMENTS 3,957,764 3/1976 Lund ................................ 260/245.2
4,089,963 5/1978 Bamberg et al. ................. 260/245.2

*Primary Examiner*—Nicholas S. Rizzo

[57] ABSTRACT

Methylacetic esters of amidinepenicillins have a powerful antibacterial effect in relation to a number of pathogenic gram-negative bacterias and to pathogenic strains of Pseudomonas. Their superiority resides in their considerably higher absorpticity in relation to that of the free acids. This invention also includes a method for the preparation of these esters by acting with chloroacetone on salts of the corresponding amidinepenicillanic acids.

7 Claims, No Drawings

ESTERS OF AMIDINEPENICILLINS

This invention relates to new methylacetic esters of amidinepenicillins with the general formula 1, wherein $R_1$ and $R_2$ are identical or different, and denote analkyl with normal or branched chain containing 1–6 carbon atoms; an alkyl containing 3–6 carbon atoms; a monocyclic or bicyclic aryl or aralkyl, preferably phenyl, benzyl, naphthyl, diphenylmethyl, phenylethyl, or naphthylmethyl; and an aralken, preferably cinnamyl, a cycloalkyl with a heterocyclic system; a heterocyclic system, preferably furyl, thienyl, pyrrolidyl, piperidyl, or morpholyl; or $R_1$ and $R_2$ together with nitrogen atom form a system of heptamethyleneimine, hexamethyleneimine, piperidine, pyrrolidine, or morpholine, non-substituted or substituted with aminoalkyl group or azidoalkyl wherein alkyl contains 1–4 carbon atoms.

The invention relates also to new addition salts of methylacetic esters of amidinepenicillins having the general formula 2, wherein $R_1$ and $R_2$ have the meaning as specified above, and Z denotes a pharmaceutically admissible organic acid, preferably tartaric, citric, oxalic, p-toluenesulphonic, or ethanedisulphonic-1,2 acid, or an anorganic acid, preferably hydrochloric, nitric, sulphuric, or phosphoric acid.

The specified amidinepenicillins in form of free acids having the general formula 3, wherein $R_1$ and $R_2$ have the meaning as specified above, are featured with very powerful antibacterial effect in relation to a number of pathogenic Gram-negative bacteriae, especially in relation to pathogenic strains of Escherichia coli, Salmonella, and Shigella (British Patent Specifications Nos. 1,293,590; 1,315,560; 1,312,050). Moreover, amidinepenicillins in form of free acids with the general formula 3, wherein $R_1$ and $R_2$ together with the nitrogen atom denote a piperidine or hexamethyleneimine system, substituted with aminoalkyl or azidoalkyl group, are featured with very powerful antibacterial effect also in relation to pathogenic strains of Pseudomonas (Belgian Patent Specification No. 856 278).

Said compounds, however, on administering per os show weak absorptivity, what considerably restricts the possibility of employing them in therapeutics.

On the other hand, it has been found that new methylacetic esters of amidinepenicillins, having the general formula 1, and addition salts thereof, having the general formula 2, manifest an absorptivity consideraby higher than that of said amidinepenicillins in form of free solids. In the blood and in constitutional liquids said esters undergo to rapid hydrolysis to free acids, and being administered per os they give both in the serum and in organs maximum levels of antibiotic, higher than those on administering equivalent doses of free acids of amidinepenicillins.

To the most active methylacetic esters of amidinepenicillins there belong methylacetic esters of 6-/N,N-1', 6'-hexyleneformamidine/-penicillanic acid having the general formula 6, and hydrochloride thereof.

By the way of example there were determined levels of free 6-/N,N,1',6'-hexyleneformamidine/-penicillanic acid in the blood serum of rats on administering per os equivalent doses (in terms of free acid):-methylacetic ester of 6-/N,N-1', 6'-hexyleneformamidine)-pencillanic acid, having the formula 6; hydrochloride of methylacetic ester of 6-/N, N-1', 6'-hexyleneformamidine/-penicillanic acid, or hydrochloride of pivaloyloxymethyl ester of 6-/N,N-1',6'-hecylaneformamidine/-penicillanic acid, introduced today to the therapeutics under the name Pivmecillinam (Table 1). From comparison of these data it results that the highest levels of free 6-/N, N-1', 6'-hexyleneformamidine/-penicillanic acid in the serum of rats is obtained on administering of methylacetic ester of 6/-N, N-1', 6'-hexyleneformamidine/-penicillanic acid, having the formula 6. The maximum levels are then over twenty times higher than those on administering of equivalent dose of corresponding free acid, and over two times higher than those on administering of equivalent dose of Pivmecillinam.

Also comparative mesurement were performed of the levels of 6-/N,N-1', 6'-hexyleneformamidine/-penicillanic acid in the blood serum, and in livers, lungs, and kidneys of rats after administration per os of equivalent doses of methylacetic ester having the formula 6 and of penicillinic preparation in form of Pivmecillinam. The results of the measurements, expressed in μg/ml are specified in Table 2.

TABLE 1

| Compound | Time | | | | | | | | | | |
|---|---|---|---|---|---|---|---|---|---|---|---|
| | 5' | 10' | 15' | 30' | 45' | 1 hr | 2 hrs | 3 hrs | 4 hrs | 5 hrs | 6 hrs |
| Methylacetic ester of 6-N,N-1', 6'-hexyleneformamidine/- penicillanic acid | 29.3 | 35.0 | 42.7 | 21.1 | 21.2 | 16.9 | 4.9 | 1.6 | 0.8 | 0.6 | 0.3 |
| Hydrochloride of methylacetic ester of 6-/N, N1', 6'-hexyleneformamidine/-penicillanic acid | 12.9 | 14.3 | 16.4 | 16.1 | 18.9 | 14.4 | 9.1 | 2.1 | 1.0 | 0.8 | 0.1 |
| Pivmecillinam | 6.3 | 12.7 | 15.5 | 19.2 | 16.3 | 14.7 | 7.9 | 2.1 | 1.8 | 1.5 | 1.1 |
| 6-/N,N-1', 6'-hexyleneformamidine/-penicillanic acid | 0.3 | 0.9 | 1.7 | 1.8 | 1.9 | 1.9 | 1.6 | 1.3 | 0.8 | 0.6 | 0.5 |

TABLE 2

| Time | Preparation | Kidneys | Lungs | Liver | Serum |
|---|---|---|---|---|---|
| 15 min. | A | 35.7 | 20.3 | 114.1 | 42.7 |
| | B | 9.9 | 23.1 | 38.3 | 42.7 |
| 30 min. | A | 32.2 | 14.2 | 78.6 | 21.2 |
| | B | 11.8 | 5.7 | 43.6 | 19.2 |
| 45 min. | A | 34.1 | 16.5 | 83.0 | 21.2 |
| | B | 9.8 | 7.0 | 50.5 | 16.3 |
| 1 hr | A | 33.2 | 11.8 | 74.2 | 16.9 |
| | B | 4.7 | 8.3 | 37.2 | 14.7 |
| 2 hrs | A | 6.7 | 3.9 | 38.1 | 4.9 |
| | B | 1.5 | 4.4 | 25.6 | 7.9 |
| 3 hrs | A | 2.7 | 1.5 | 11.3 | 1.6 |
| | B | 0.29 | 0.76 | 6.6 | 2.1 |
| 4 hrs | A | 0.5 | 1.2 | 4.3 | 0.8 |
| | B | 0.27 | 1.19 | 8.4 | 1.8 |
| 6 hrs | A | 0.3 | 0.7 | 1.4 | 0.3 |

TABLE 2-continued

| Time | Preparation | Kidneys | Lungs | Liver | Serum |
|------|-------------|---------|-------|-------|-------|
|      | B           | 0.36    | 0.8   | 3.1   | 1.1   |

A = methylacetic ester of 6-/N, N-1', 6'- hexyleneformamidine/ -penicillanic acid
B = Pivmecillinam The presented data prove that after administration of methylacetic ester of 6-/N, N-1', 6'-hexyleneformamidine/-penicciliinic acid, having the formula 6, high levels of free acid are obtained both in the blood serum and in the investigated organs. Maximum levels are considerably higher than those observed after administration of equivalent dose of Pivmecillinam, that is in kidneys three times, and in the liver over two times higher. The maximum levels in the lungs, instead, on administering equivalent doses of both preparations are approximate ones.

Also after administration per os of dihydrochloride of methylacetic ester of 6-{N, N-[3'-(γ-aminopropylo/-1', 5'-pentyleneformamidine)]}-penicillanic acid the levels of free acid are obtained in the serum and in organs of rats, being multiply higher than those on administering an equivalent dose of corresponding free acid.

Moreover, methylacetic esters of amidinepenicillins, having the general formula 1, and addition salts, having the formula 2, are featured with very low toxicity. For instance the methylacetic ester of 6-(N,N-1', 6'-hexyleneformamidine)-penicillanic acid, having the formula 6, and addition salts thereof, show a toxicity lower than that of Pivascillinam. After administration per os of the ester having the formula 6 the value $LD_{50}$, as determined on mice, amounts to over 3 g/kg of the body weight, and $LD_{50}$ of the hydrochloride of said ester amounts over 5 g/kg of the body weight, whereas $LD_{50}$ determined under the same conditions for Pivascillinam amounts to 2,6 g/kg of the body weight.

An additional advantage consists therein that said methylacetic ester with the formula 6 and hydrochloride thereof, on the contrary to Pivmecillinam, show no effect onto the arterial pressure of experimental animals. The subject of the invention there are also processes of production of new methylacetic esters of amidinepenicillins with the formula 1, wherein $R_1$ and $R_2$ have the meaning as specified above, and of addition salts thereof with pharmaceutically admitted acids having the formula 2. Said compounds are produced by acting with chloroacetone onto the salts of corresponding amidinepenicillanic acids, having the general formula 3, wherein $R_1$ and $R_2$ have the meaning as specified above, with organic or anorganic bases, for instance onto sodium salts, potassium salts, or salts with tertiary amine. As tertiary amine preferably triethylamine, N-ethylpiperidine, or N-methylmorpholine. The reaction is conducted in a neutral organic solvent, for instance in dimethylformamide, dimethyl sulphoide, or dimethyl acetamide. As substrate isolated amidinepenicillins are employed, or a reaction mixture containing salts of amidinepenicillins. Such mixture can be obtained for instance in results of reaction of corresponding salt of 6-aminopenicillanic acid with active derivates of amides (British Patent Specification No. 1,417,099). The obtained product is isolated from the mixture after the reaction in form of free ester or its addition salt with acid. In case of obtaining of free ester it can be subsequently converted into addition salt. An advantage of this method is a simplicity of chemical operations with simultaneous achieving of high product yields.

The compounds having the general formula 1 and addition salts thereof, with the general formula 2, can be also obtained in result of condensation of methylacetic ester of 6-amidinepenicillanic acid having the formula 4 with corresponding active derivate of N-formylamine having the general formula 5, wherein $R_1$ and $R_2$ have the meaning as specified above, in the presence of tertiary amine in an inert organic solvent. The initial methylacetic ester of 6-aminepenicillanic acid can be obtained in the process disclosed in the British Patent Specification No. 1,164,457. This ester is employed in free form or in form of an addition salt with organic acid, especially p-toluenesulphonic acid. An active derivate of N-formylamine having the general formula 5 constitutes a suitable chloroformiminic chloride, a complex with dimethyl sulphate, or acetal. Said compounds are known and described in the literature.

The condensation reaction is conducted in the presence of tertiary amine, preferably triethylamine, N-Methylpiperidine, N-ethylpiperidine, or N-methylpirolidine.

As inert organic solvent especially chloroform or methylene chloride are used. The obtained product gets isolated from the reaction mixture in form of free ester or in form of addition salt with acid. In case of free ester it can be subsequently converted into its addition salt.

An advantage of production of methylacetic esters of amidinepenicillins is a considerably lower cost and easier accessibility of the substrate/methylacetic ester of 6-aminepenicillanic acid with the formula 4/, and thus lower cost of the final compound.

For obtaining addition salts of methylacetic esters of amidinepenicillins with the general formula 2 as organic acids there are employed advantageously tartaric, citric, exalic, acetic, p-toluenesulphonic, or ethanedisulphonic-1,2 acid, and as anorganic acids -hydrochloric, sulphuric, nitric, or phosphoric acid. The addition salts are produced in the medium of an organic solvent, especially of an alcohol containing 1–5 carbon atoms, or of ether, for instance diethyl, dipropyl, diisobutyl, or dibutyl ether. The obtained salt is then isolated after known methods.

With respect to interesting pharmacological properties thereof, and simplicity of their production, the compounds according to the invention can find a broad application in the therapy for controlling the infections caused by Gram-negative bacterise.

The methods of obtaining of new methylacetic esters of amidinepenicillins and of their addition salts are explained by following examples, which do not restrict the scope of the invention.

EXAMPLE I 7.52 g/0.02 mole/ of 6-/N,N-1',6'-hexyleneformamidine/-penicillanic acid is suspended in 30 ml of dry N,N-dimethylformamide. After cooling down to the temperature of 0° C. 2.8 ml /0.02 mole/ of triethylamine are added, and under intensive stirring 3.4 ml (0.04 mole) of chloroacetone are added drop by drop, whereafter the mixture is stirred for 5 hours at the temperature of 0° C. and allowed to stay by night in a refrigerator. Then the reaction mixture is poured, under intensive stirring, into 400 ml of water with salt at the temperature of 0°–5° C., brought to the pH-value of 8.0–8.5, the isolated deposit is then filtered, washed with cold water (3×50 ml) and dried above $P_2O_5$. There are obtained 6.6 g of raw methylacetic ester of 6-/N,N-1', 6'-hexyleneformamidine/-penicillanic acid, what corresponds with 86% of theoretical yield. The raw ester is crystallized from n-amyl alcohol, resulting in a preparation having the form of white glittering needles having the melting point of 79°–80° C. The spectrum in infrared shows characteristic bands at 1770 cm$^{-1}$ (C=O β-lactam), 1740 and 1720 cm$^{-1}$ (C=O, ester), 1620 cm$^{-1}$ (C=N).

In the NMR spectrum, recorded in DMSO at 60 MHz, the following bands are observed—(in ppm)
1.47 s, (3H), 1.59 s (3H), two groups CH$_3$ at C-2
1.3–1.7 m, (8H), —(CH$_2$)$_4$—from the hexamethyleneimine system.
2.06 s, (3H), group CH$_3$—from CH$_3$COCH$_2$—3.1–3.4 m, (4H), —CH$_2$—N—CH$_2$—,
4.18 s, (H), C-3
4.76 s, (2H) group CH$_2$—from CH$_3$COCH$_2$—
4.9 d, (H), C-6, J=4
5.3 d, (H), C-5, =JH=4
7.4 s, (H), —N=CH—N—.

EXAMPLE II

Conducting the reaction as in Example I, but using an equivalent amount of dimethylsulphoxide instead of dimethylformamide, raw methylacetic ester of 6-/N,N-1',6'-hexyleneformamidine/-penicillanic acid is obtained with a yield of 84% of theoretical yield.

EXAMPLE III 3.8 g /0.01 mole/ of methylacetic of 6-/N,N-1',6'-hexyleneformamidine/-penicillanic acid is suspended in 13 ml of anhydrous isopropyl alcohol, and at the temperature of 0°–5° C. in course of 2–3 min there are added drop by drop 4 ml (0.01 mole) 2.5 n solution of HCl in isopropanol. Then 30 ml of ether are added and allowed to stay in a refrigerator for 18 hours.

The isolated deposit is filtered, washed two times with ether, dried above P$_2$O$_5$, and crystallized from anhydrous isopropanol. Hydrochloride of the initial ester is obtained in form of white glittering needles with a yield amounting to 85% in terms of used ester.

The infrared spectrum shows characteristic bands at 1780 cm$^{-1}$ (C=O, β-lactam), 1755, 1730 cm$^{-1}$ (C=O, ester), 1665 cm$^{-1}$ (C=N).

In the NMR spectrum recorded in D$_2$O at 60 MHz following bands are observed (in δppm):
1.52 s (3H), 1.76 s (3H), two groups CH$_3$ at C-2 1.4–2.0 m, (8H), —(CH$_2$/4)—from the hexamethylene—imine system
2.26 s, (3H), group CH$_3$—from CH$_3$COCH$_2$—
3.5–4.0 m, (4H), —CH$_2$—N—CH$_2$—
4.15 s, (H), C-3
5.55 d, (H), C-6, J=4
5.73 d, (H), C-5, J=4
8.13 s, (H), —N=CH—N—.

EXAMPLE IV

Proceeding similarly as in Example III, but using equivalent amounts of sulphuric acid solution, sulphate of methylacetic ester of 6-/N,N-1',6'-hexyleneformamidine/-penicillanic acid is obtained, with an yield of 78%.

The infrared spectrum shows characteristic bands at 1775 cm$^{-1}$ (C=O, β-lactam), 1760, 1735 cm$^{-1}$ (C=O, ester), 1665 cm$^{-1}$ (C=N).

EXAMPLE V

Proceeding similarly as in Example III, but using an equivalent amount of phosphoric acid solution, phosphate of methylacetic ester of 6/N,N-1',6'-hexyleneformamidine/-penicillanic acid is obtained with a yield of 81%.

The infrared spectrum shows characteristic bands at 1780 cm$^{-1}$ (C=O, β-lactam), 1755, 1730 cm$^{-1}$ (C=O, ester), 1670 cm$^{-1}$ (C=N).

EXAMPLE VI

Proceeding similarly as in Example III, but using an equivalent amount of the solution of ethanedisulphonic-1,2 acid, ethanedisulphonate-1,2 of methylacetic ester of 6-/N,N-1',6'-hexyleneformamidine/-penicillanic acid is obtained with a yield of 73%.

The infrared spectrum shows characteristic bands at 1775 cm$^{-1}$ (C=O, β-lactam), 1755, 1730 cm$^{-1}$ (C=O, ester), 1675 cm$^{-1}$ (C=N).

EXAMPLE VII

Proceeding similarly as in Example I, but using an equivalent amount of 6-/N,N-diethylformamidine/-penicillanic acid, methylacetic ester of 6-/N,N-diethylformamidine/-penicillanic acid is obtained with a yield of 55%.

The infrared spectrum shows characteristic bands at 1775 cm$^{-1}$ (C=O, β-lactam), 1735, 1720 cm$^{-1}$ (C=O, ester), 1625 cm$^{-1}$ (C=N).

In the NMR spectrum registered in DMSO at 60 MHz following bands are observed (in δ ppm):
1.48 s, (3H), 1.60 s, (3H), two groups CH$_3$—at C-2
1.0–1.7 (multiplet covering the bands of groups CH$_3$—at C-2) (6H), two groups CH$_3$ from CH$_3$CH$_2$NCH$_2$CH$_3$
3.7–3.9, (4H), two groups CH$_2$—from CH$_3$CH$_2$NCH$_2$CH$_3$
4.4 s, (H), C-3
4.88 s, (2H), group CH$_2$—from CH$_3$COCH$_2$—
5.1 d, (H), C-6, J=4
5.5 d, (H), C-5, J=4
7.85 s, (H), N=CH—N.

EXAMPLE VIII 21.6 g (0.1 mole) of 6-aminopenicillanic acid are suspended in 100 ml of methylene chloride, then 32.8 ml (0.23 mole) of triethylamine are added and stirred for 1.5 hour at room temperature. Then the mixture is cooled down to the temperature of 0°–5° C., and slowly 32 g (0.12 mole) of a complex of N-formylhexamethyleneimine with dimethyl sulfate are added drop by drop and stirred for further 2 hours, increasing the temperature gradually up to 20° C. After thorough evaporation of the solvent, to the remainder 60 ml of dimethylformamide are added, cooled down to 0° C. 16.8 ml (0.2 mole) of chloroacetone are added drop by drop, the mixture is stirred 3 hours, and then is allowed to stand for further 18 hours at the temperature of 0°–5° C. The reaction mixture is dropped into 600 ml of cold brine and stirred for 0.5 hour. The isolated deposit of ester, of cream colour, is filtered, and washed with cold water and petroleum benzin. After drying in the air there are obtained 24 g of methylacetic ester of 6-/N,N-1',6'-hexyleneformamidine/-penicillanic acid, what makes 63% of theoretical yield in terms of 6-aminopenicillanic acid.

After crystallization from n-amyl alcohol the ester is obtained in form of white glittering needles having the melting point of 79°–80° C.

The infrared and NMR spectrum show a good conformity with those of the ester obtained after the method specified in example I.

EXAMPLE IX

Proceeding similarly as in Example VIII but using an equivalent amount of complex of N-formyl-N-methylbenzylamine with dimethyl sulphate methyl-acetic ester of 6-/N-methyl-N-benzyloformamidine/-penicillanic acidins obtained with a yield of 58% in terms of 6-aminopenicillanic acid.

The infrared spectrum shows characteristic bands at 1765 cm$^{-1}$ (C=O, $\beta$-lactam), 1740, 1720 cm$^{-1}$ (C=O, ester), 1625 cm$^{-1}$ (C=N).

In the NMR spectrum recorded in DMSO at 60 MHz there are observed the following bands (in $\delta$ppm):
1.58 s, (3H), 1.62 s, (3H), two groups CH$_3$—at C-2
2.16 s, (3H) group CH$_3$13 from CH$_3$COCH$_2$—
2.76 s, (3H), group CH$_3$—from CH$_3$N—
4.38 s, (H), C-3
4.45 s, (2H), group CH$_2$—from C$_6$H$_5$CH$_2$—
4.90 s, (2H), group CH$_2$—from CH$_3$COCH$_2$—
5.15 d, (H), C-6, J=4
5.50 d, (H), C-5, J=4
7.2–7.6 m, (5H), C$_6$H$_5$—
7.88 s, (H), N=CH—N.

EXAMPLE X

Proceeding similarly as in Example VIII, but using an equivalent amount of the complex of N-formyl-N-methylcyclohexylamine with dimethyl sulphate methyl acetic ester of 6-/N-methyl-N-cyclohexylformamidin/-penicillanic acid with a yield of 55% in terms of 6-aminopenicillanic acid.

The infrared spectrum shows characteristic bands at 1770 cm.$^{-1}$ (C=O, $\beta$-lactam), 1745, 1720 cm$^{-1}$ (C=O, ester), 1625 cm$^{-1}$ (O=N).

In the NMR spectrum registered in DMSO at 60 MHz there are observed the following characteristic bands (in $\delta$ ppm):
1.60 s, (3H), 1.72 s, (3H), two groups CH$_3$—at C-2
1.0–2.0 m, protons of cyclohexyl system
2.18 s, (3H), group CH$_3$—from CH$_3$COCH$_2$—
2.92 s, (3H), group CH$_3$—from CH$_3$N—
3.65 m, (H), CHN—from the cyclohexyl system
4.48 s, (H), C-3
4.96 s, (2H), group CH$_2$—from CH$_3$COCH$_2$—
5.38 d, (H), C-6, J=4
5.55 d, (H), C-5, J=4
8.0 s, (H), N=CH—N

EXAMPLE XI

Proceeding similarly as in Example I, but using an equivalent amount of 6-{N,N-[3'-($\gamma$-azidopropyl)-1',5'-pentyleneformamidine]}-penicillanic acid, it is obtained methylacetic ester of 6-{N,N-[3'-($\gamma$-azidopropyl)-1',5'-pentileneformamidine]}-penicillanic acid, with a yield of 65%.

After reduction with hydrogen, using a palladium catalyst in a acidic medium, it is obtained the dihydrochloride of ester methylacetic of 6-{N,N-[3'-($\gamma$-aminopropyl)-1',5'-pentileneformamidine]}-penicillanic acid.

The infrared spectrum shows characteristic bands at 1770 cm$^{-1}$ (C=O, $\beta$-lactam), 1745, 1715 cm$^{-1}$ (C=O, ester) 1685 cm$^{-1}$ (C=N).

In the NMR spectrum recorded in D$_2$O at 60 MHz the following characteristic bands are observed (in d ppm):

1.59 s, (3H), 1.75 s, (3H), two groups CH$_3$- at C-2'
1.0–2.0 m, (9H), -CH$_2$-CH-CH$_2$ from the piperidine system and -CH$_2$-CH$_2$ from the group NH$_2$-CH$_2$-CH$_2$-CH) 2.23 s, (3H), group CH$_3$- from CH$_3$COCH$_2$- 2.9–4.1 m, (6H), group CH$_2$ from NH$_2$-CH$_2$- an -CH$_2$-N-CH$_2$-
4.66 s, (H), C-3 5.02 s, (2H), group CH$_2$- from CH$_3$COCH$_2$-
5.51 d, (H), C-6, J=4
5.68 d, (H), C-5, J=4
8.0 s, (H), -N-CH=N-.

EXAMPLE XII 8.8 g (0.02 mole) of p-toluenesulphonate of methylacetyl ester of 6-aminepenicillanic acid are added to 100 ml of chloroform (dry) and after cooling down to the temperature of −30° C. a solution of 0.02 mole of (N,N-1,6-hexylene/chloroforminiate chloride in 20 ml of chloroform is added drop by drop under stirring. Then 8.4 ml (0.06 mole) of triethylamine is added and stirred for 2 hours, increasing the temperature gradually up to 0° C. The obtained solution is washed two times with water, then dried by means of Na$_2$SO$_4$, and thickened. The obtained remainder is washed three times with petroleum benzine and dried in the air. The raw product is crystallized from n-amyl alcohol, what results in obtaining of 4.1 g of pure methylacetyl ester of 6-/N,N-1',6'-Hexyleneformamidine/-penicillanic acid, what constitutes 53.9% of theoretical yield. The melting point equals to 78°–79° C.

The infrared and NMR spectra show a conformity with these of the ester received after the method specified in Example I.

EXAMPLE XIII

Proceeding analogically as in Example XII, but using an equivalent amount of /N,N-diethyl/-chloroformiminiate chloride methylacetyl ester of 6/N,N-diethylformamidine/-penicillanic acid is obtained.

The infrared and NMR spectra show a conformity with these of the ester obtained after the method specified in Example VII.

EXAMPLE XIV

Proceeding analogically as in Example XII, but using an equivalent amount of /N-methyl-N-cyclohexyl/-chloraformiminic chloride methylacetyl ester of 6-/N-methyl-N-cyclohexylformamidine/-penicillanic acid is obtained. The infrared and NMR spectra show a conformity with those of the ester obtained after the method specified in Example X.

EXAMPLE XV

Proceeding analogically as in Example XII, but using an equivalent amount of /N-methyl-N-benzyl/-chloroformiminic chloride methylacetyl ester of 6-/N-methyl-N-benzylformamidine/-penicillanic acid is obtained.

The infrared and NMR spectra show a conformity with those of the ester obtained after the method specified in Example IX.

EXAMPLE XVI

Proceeding analogically as in Example XII, but using an equivalent amount of {N,N-[3'-($\gamma$-azidepropyl/-1',5'-pentylene]}-chloroformiminic chloride methylacetyl ester of 6-{N,N-[3'-($\gamma$-azidepropyl)-1',5'-pentyleneformamidine]}-penicillanic acid is obtained.

After reduction with hydrogen, using palladium catalyst in acidic medium, dihydrochloride of methylacetyl ester of 6-N,N-[3'-(γ-aminopropyl)-1', 5'-penteneformamidine]-penicillanic acid is obtained.

The infrared and NMR spectra show a conformity with those of the ester obtained after the method specified in Example XI.

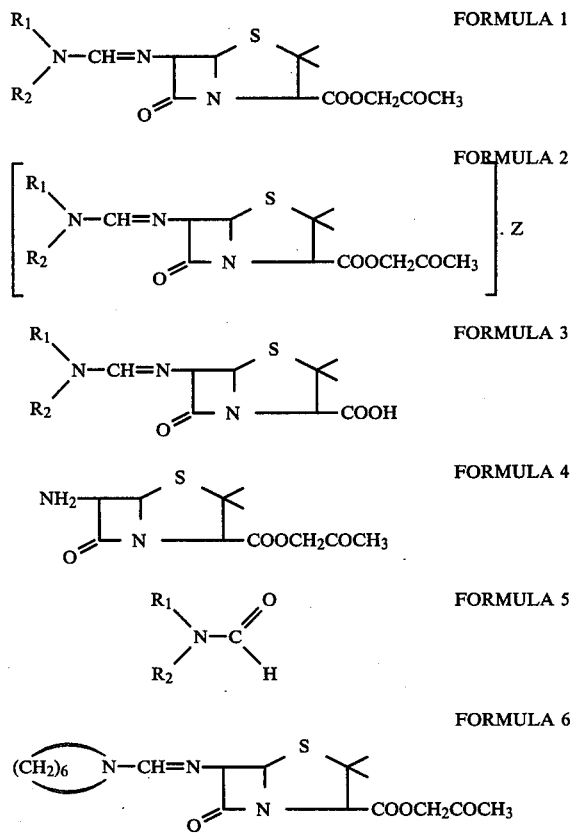

What is claimed is:

1. Acetylmethyl esters of amidinopenicillins of the formula

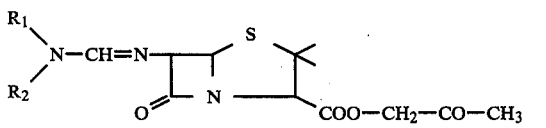

wherein each of $R_1$ and $R_2$, which are the same or different,
is selected from the group consisting of a straight or branched chain alkyl group containing from 1 to 6 carbon atoms, which may be substituted with a radical selected from the group consisting of a cycloalkyl group containing from 5 to 7 carbon atoms; an alkenyl group containing from 3 to 6 carbon atoms; an aryl group selected from the group consisting of phenyl, benzyl, naphthyl, phenylethyl, diphenylmethyl, naphthylmethyl and cinnamyl groups; and a heterocyclic group selected from the group consisting of furyl, thienyl, pyrrolidyl, piperidyl and morpholinyl; or $R_1$ and $R_2$ together with the adjacent nitrogen atom form a heptamethyleneimine, hexamethyleneimine, piperidine, pyrrolidine or morpholine ring system, unsubstituted or substituted with an aminoalkyl or azidoalkyl group, wherein the alkyl group contains up to 4 carbon atoms; and addition salts thereof of the formula

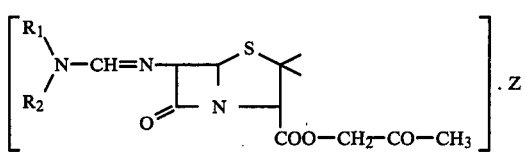

wherein $R_1$ and $R_2$ are as defined above, and Z is a pharmaceutically acceptable organic or inorganic acid.

2. Methylacetyl ester of 6-/N,N-1',6'-hexyleneformamidine/-penicillanic acid, and addition salts thereof with pharmaceutically acceptable organic or inorganic acids.

3. Hydrochloride of methylacetyl ester of 6-/N,N-1',6'-hexyleneformamidine/-penicillanic acid.

4. Methylacetyl ester of {6-N,N-[3'-(γ-azidepropyl)-1',5'-pentyleneformamidine]}-penicillanic acid and addition salts thereof with pharmaceutically acceptable organic or inorganic acids.

5. Methylacetyl ester of 6-{N,N-[3'-(γ-aminopropyl)-1',5'-pentyleneformamidine]}-penicillanic acid, and addition salts thereof with pharmaceutically acceptable organic or inorganic acids.

6. Dihydrochloride of Methylacetyl ester of 6-{N,N-[3'-(γ-aminopropyl)-1',5'-pentyleneformamidine]}-penicillanic acid.

7. The process of combatting the effects of pathogenic gram negative bacteriae in mammals which comprises administering thereto an antibacterially effective amount of an acetylmethyl ester of amidinopenicillins of the formula

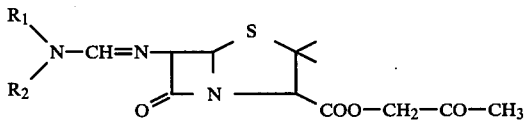

wherein each of $R_1$ and $R_2$, which are the same or different, is selected from the group consisting of a straight or branched chain alkyl group containing from 1 to 6 carbon atoms, which may be substituted with a radical selected from the group consisting of a cycloalkyl group containing from 5 to 7 carbon atoms; an alkenyl group containing from 3 to 6 carbon atoms; an aryl group selected from the group consisting of phenyl, benzyl, naphthyl, phenylethyl, diphenylmethyl, naphthylmethyl and cinnamyl groups; and a heterocyclic group selected from the group consisting of furyl, thienyl, pyrrolidyl, piperidyl and morpholinyl; or $R_1$ and $R_2$ together with the adjacent nitrogen atom form a heptamethyleneimine, hexamethyleneimine, piperidine, pyrrolidine or morpholine ring system, unsubstituted or substituted with an aminoalkyl or azidoalkyl group, wherein the alkyl group contains up to 4 carbon atoms; and addition salts thereof of the formula

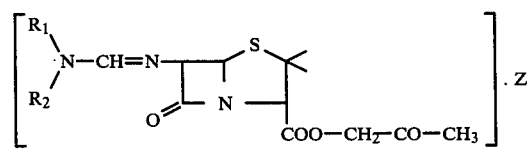

wherein $R_1$ and $R_2$ are as defined above, and Z is a pharmaceutically acceptable organic or inorganic acid.

* * * * *